United States Patent [19]

Gross

[11] Patent Number: 5,053,015
[45] Date of Patent: Oct. 1, 1991

[54] LOCKING CATHETER ADAPTER

[75] Inventor: James R. Gross, Geneva, Ill.

[73] Assignee: The Kendall Company, Mansfield, Mass.

[21] Appl. No.: 400,859

[22] Filed: Aug. 30, 1989

[51] Int. Cl.[5] .............................................. A61M 5/178
[52] U.S. Cl. .................................... 604/167; 604/243; 604/256; 604/283
[58] Field of Search ......................... 604/178, 240–243, 604/167, 169, 256, 283, 905; 285/321, 330, 360, 386, 921; 138/96 T

[56] References Cited

U.S. PATENT DOCUMENTS

| | | | |
|---|---|---|---|
| 1,253,065 | 1/1918 | Looze | 285/360 |
| 4,187,848 | 2/1980 | Taylor | 604/280 |
| 4,613,329 | 9/1986 | Bodicky | 604/158 |
| 4,842,592 | 6/1986 | Caggiani et al. | 604/283 |
| 4,857,062 | 8/1989 | Russell | 604/256 |
| 4,929,243 | 5/1990 | Koch et al. | 604/283 |

Primary Examiner—John D. Yasko
Assistant Examiner—Anthony Gutowski
Attorney, Agent, or Firm—Alvin Isaacs

[57] ABSTRACT

A unitary adapter is disclosed for placing a catheter in fluid communication with a syringe or other source of liquid medication. The adapter has a catheter connector for releasably securing the proximal end of a catheter extending from a patient's body and a connector releasably engaging the liquid medication source, the connectors being attached to one another and movable between an open position for inserting the catheter end and a closed position for securing the catheter end within the connector.

The adapter is designed to prevent accidental opening and the resulting falling out of the catheter when the connectors are in the closed position.

8 Claims, 2 Drawing Sheets

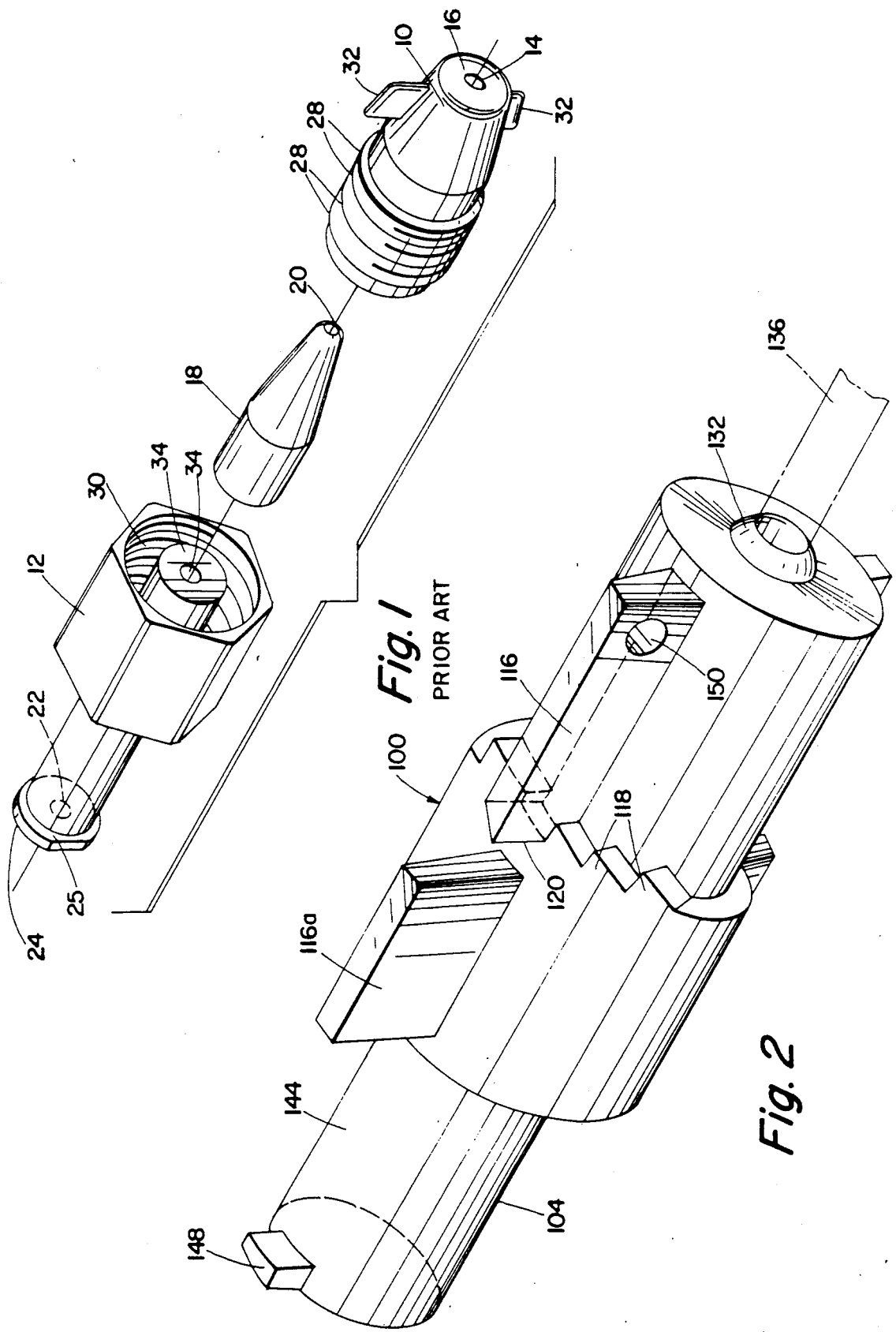

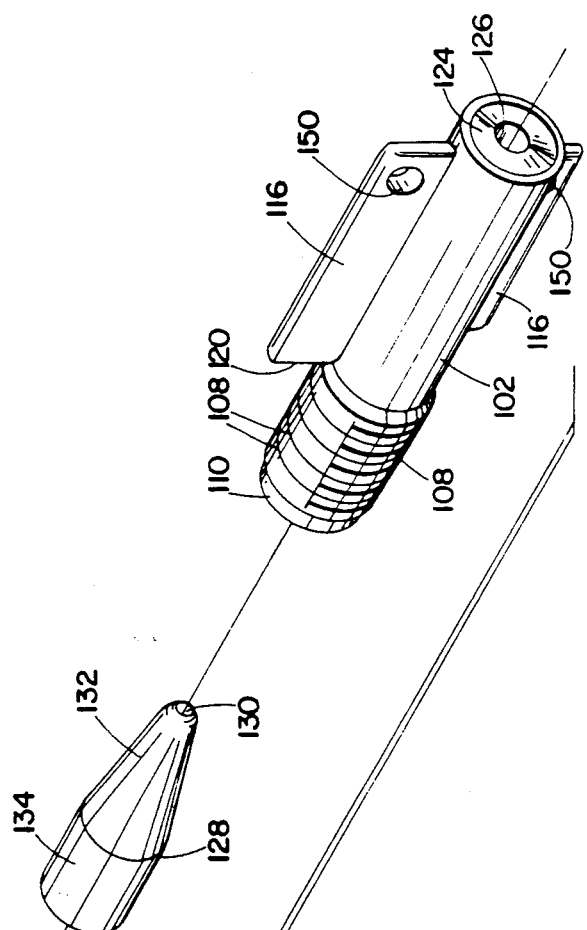
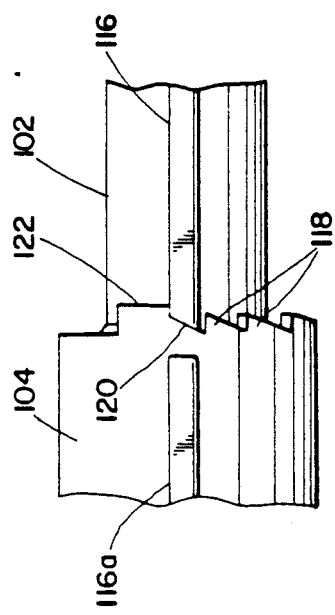
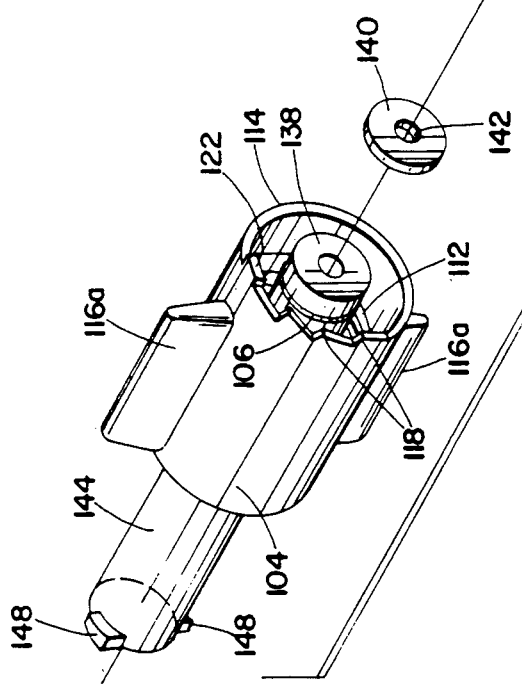
Fig. 4
Fig. 3

LOCKING CATHETER ADAPTER

BACKGROUND OF THE INVENTION

Continuous spinal anesthesia procedures and continuous epidural anesthesia procedures are of course well known in the art. In either case, the distal end of the catheter is first introduced in to the patient's body with the proximal or trailing end outside the body to receive the anesthetic.

To do so, an adapter is employed connecting the proximal end of the catheter at one end of the adapter to a source of liquid anesthetic, e.g. a syringe, at the other. The adapter has a channel communicating with the catheter end so that when the liquid anesthetic is introduced into the channel, it passes through the catheter into either the subarachnoid space, if the spinal anesthesia procedure is used or into the epidural space, as would be the case with the epidural anesthesia procedure.

As an illustration of prior adapters for this purpose, mention may be made of those described and claimed in U.S. Pat. No. 4,187,848 issued to Glenn N. Taylor. As disclosed therein, the adapter comprises two separate members, one being designated as the body member, the other being termed a compression member. The body member has an elongated bore and an opening at its distal end for receiving the proximal end of the catheter extending from the patient's body. An elongated elastic plug having a channel extending therethrough is seated in uncompressed condition within the bore of the body member, the channel being aligned with the opening of the body member so that the catheter end inserted in the opening can be positioned within the plug channel. The compression member has a port at its proximal end where the tip of a syringe may be releasably engaged for injecting liquid anesthetic. A passageway for fluid extends between the two ends of the compression member so that when the proximal end of the body member and the distal end of the compression member are secured together, the liquid anesthetic injected from the syringe may be pumped into the catheter. To connect the two members, the proximal end of the body member is provided with external threads and the distal end of the compression member with internal threads mating with the body member threads. When the threads are tightened to secure the two members, the plug is compressed to retain the catheter end positioned therein.

While a catheter adapter of this general description is in theory entirely satisfactory for connecting the catheter to the syringe, the prior art two-piece adapters currently in use, as exemplified by the teachings of the aforementioned patent, do nevertheless suffer from certain inherent disadvantages.

A primary disadvantage is that there is no locking engagement to maintain the two components together, as intended. Consequently, there is a danger for unscrewing or back-off, resulting in loss of compressive force on the plug and, consequently, in separation of the catheter from the adapter.

Another problem which occurs from time-to-time is the human error in attempting to screw the two components together. It sometimes happens that one of the components is dropped. This human error necessitates the time and expense of opening a whole new sterile tray to replace the dropped component.

It is accordingly the task of this invention to provide an improved adapter which will obviate the aforementioned problems.

BRIEF DESCRIPTION OF THE INVENTION

In accordance with the present invention, this task is solved in a simple and elegant manner by providing a unitary adapter having one component for releasably engaging the syringe or other source of liquid medication, a second component for securing the catheter end, the two components being attached together with the distal end of the first component in superposition with the proximal end of the second component so as to prevent accidental dropping of either component, the respective components further being movable between an open position for inserting the catheter in the adapter and a closed position for retaining the catheter in place, and means for locking the adapter in the closed position to prevent drop-off.

BRIEF DESCRIPTION OF THE DRAWINGS

FIG. 1 is a fragmentary, exploded elevational view of a two-piece catheter adapter illustrative of the current state of the art;

FIG. 2. is a perspective view illustrating the novel adapter of this invention;

FIG. 3 is an exploded elevational view of the novel catheter of FIG. 2; and

FIG. 4 is a fragmentary top view illustrating the locking mechanism for securing the adapter in the closed position, as shown in FIG. 2.

DETAILED DESCRIPTION OF THE INVENTION

As mentioned, adapters for continuous spinal or epidural catheters currently in use are of a two-piece construction.

FIG. 1, which need not be described in great detail for purposes of understanding the nature and objects of this invention, is illustrative of the adapters presently in use for the administration of spinal anesthesia.

As shown therein, the adapter consists of two separate body members which, for ease of reference, will be designated as catheter connector 10 and syringe connector 12. Both connectors have a longitudinally extending passageway for pumping the anesthetic from the syringe into the catheter. Catheter connector 10 has an opening 14 at its distal end 16. A compressible plug 18 of elastomeric material having a longitudinally extending channel 20 is seated within a correspondingly shaped bore within connector 10 in a relatively uncompressed condition with channel 20 aligned with opening 14 to receive the proximal end of a catheter (not shown) extending from the body of a patient.

Syringe connector 12 has a tapered port 22 at its proximal end 24 to receive the tip of a syringe (not shown). The proximal end 24 has luer lock flanges 25 and a female luer slip 26 adapted to receive the luer tip of the syringe so that the syringe may be releasably locked to connector 12.

Connector 10 has external threads 28 adjacent its proximal end which mate with internal threads 30 adjacent the distal end of syringe connector 12.

When the respective connectors are screwed together, e.g. by rotating wings 32 on catheter connector 10, a compression collar 34 having an opening 36 compresses plug 18 to decrease the external dimensions (gap) of channel 20 to secure the catheter end in the adapter.

In use, the distal end of the catheter is first positioned in the patient in per se known manner. The proximal end of the catheter is inserted in the catheter connector and the two connectors are then screwed tightly together to "lock" the catheter in the adapter. The anesthesia procedure may then commence by engaging the syringe in the syringe connector and injecting the liquid anesthetic.

A major disadvantage in adapters of this general description is the tendency for back-off wherein the threads loosen or unscrew to release the compressive force sufficiently for the catheter to be displaced from the adapter. [Since the compression applied should never be so great as to materially narrow the gap of the catheter, substantial drop in compressive force is not required for loss of the catheter connection to occur.]

Another problem is the human factor involved in screwing the two separate connectors together. The parts are relatively small and extremely light. It is very easy to drop one or the other during the manual manipulative step of joining them together. If this should occur, the rigid operating room requirements for aseptic instruments demands that the dropped connector be discarded. This in turn requires the time and expense of opening a new sterile spinal tray to obtain a replacement.

The present invention is directed to a novel adapter which obviates these problems.

Stated simply, in accordance with this invention, the adapter is of a one-piece or unitary construction wherein the catheter connector and syringe connector are movably pre-connected with respect to each other from an open position to insert the catheter end and a closed position to secure the catheter in place. Anti-back-off means are provided to retain the connectors in the closed position, thereby locking the catheter end in the adapter until released by disengaging the anti-back-off means.

In the preferred embodiment, means are also provided for preventing overtightening of the connectors, which overtightening will cause excessive compressive force to be exerted on the catheter, causing unwanted lowering of its gap through which the anesthetic must traverse as well as possible damage to the catheter.

FIGS. 2 and 3 illustrate the novel adapter of this invention.

As shown, adapter 100 has a catheter connector housing 102 (similar to that shown in FIG. 1) and a syringe connector housing 104 which are secured in juxtaposition as a unitary device by means of an external snap ring 106 which engages an internal snap ring (not shown) at the proximal end 110 of catheter connector 102 to prevent separation of the respective housings.

Catheter connector 102 has a series of external threads 108 adjacent its proximal end 110 which mate with internal threads 112 at the distal end 114 of the syringe connector housing 104. By tightening or loosening the connection, e.g. by gripping one of wings 116 or 116a and rotating the other, the connectors are movable longitudinally with respect to each other from a closed position wherein all the threads are engaged (to secure the catheter) to an open position (for insertion or removal of the catheter, as the case may be). When in the open or unthreaded position, the connectors are retained together by snap ring 106, as previously mentioned.

As seen, a portion of distal end 114 of the syringe connector has teeth 118. When screwed together, a locking wing edge 120 interferes with a course of the ratchet-type teeth 118, preventing the connectors from accidentally unscrewing and thereby releasing the catheter from connector 102. In other words, the teeth cooperate with the locking wing edge 120 to prevent back-off and thus lock the respective connectors in the closed position until intentionally disengaged to release the catheter. To prevent overtightening which could cause detrimental excessive compression to be exerted on the catheter, a full stop detent member 122 is preferably provided.

As was the case with the prior art adapters such as illustrated in FIG. 1, catheter connector 102 is generally cylindrical and has an elongated bore. The distal end 124 has a central opening or port 126 through which the proximal (training) end of a catheter extending from the patient's body may be inserted.

An enlongated plug 128 of elastomeric material (e.g. natural rubber, synthetic rubber, or an elastomeric polymer such as one of the KRATON (trademark of Shell Chemical Company) series having a channel 130 is seated within connector 102. Plug 128 has a distal conical section 132 and a proximal cylindrical section 134. The portion of the bore in which the plug is to be received with the end of the cone adjacent opening 126 is of like configuration so that the plug is positioned therein in relatively uncompressed condition with channel 130 aligned with opening 126. Both opening 126 and channel 130 (when the latter is uncompressed) have inner dimensions slightly larger than the outer dimensions of the catheter 136 (FIG. 2) to permit easy insertion through the opening and then into the plug.

When the proximal end of the catheter is so positioned, the wings 116 or 116a are rotated to place the adapter in the closed position with the locking wing edge 120 of the catheter connector abutting detent member 122. In this closed position, teeth 118 lock the two connectors together to prevent loosening or back-off. In this position, compression collar 138 located at the distal end of syringe connector housing 104 applies compressive force to the proximal end of plug 128, causing it to compress longitudinally to narrow the gap of channel 130, thereby tightly frictionally engaging catheter 130 positioned therein. To prevent damage to the proximal end of the channel 124 in the plug, a slip washer 140 is preferably provided. As seen in FIG. 2, when the plug is compressed, the tip of conical section 132 extrudes through opening 126, thereby providing a liquid-tight strain relief collar for the catheter.

Compression collar 138 has an opening 142 communicating with a fluid passageway within connector 104 and aligned with washer 140 and channel 130, thereby providing a channel for anesthetic injected into the proximal end of syringe connector 104 to bumped through the adapter and then into the patient via the positioned catheter for administration of the anesthesia procedure.

To accomplish the anesthesia procedure, syringe connector 104 has a female luer slip 144 to receive the tip of the syringe and to frictionally engage the syringe luer when inserted therein. Luer locking wings 148 are provided for engagement to luer locking syringes.

The materials which may be utilized in the manufacture of the adapter of this invention will be readily apparent to those skilled in the art and as such will be a matter of individual choice. Accordingly, they are not critical and per se comprise no part of this invention. In general, with the exception of the elastomeric plug, any of the known plastics which are substantially rigid and of medical grade for use in surgical procedures may be utilized.

In like manner, the method of manufacture will be readily suggested and is accordingly not a part of this invention. Injection molding or any of the other known industrial manufacturing techniques may be employed.

It will be appreciated that the foregoing description is by way of illustration only and that various changes, modifications and additions may be made without departing from the scope of the invention herein contemplated.

For example, while not necessary in the practice of this invention, the wings 116 on connector 102 are shown to have holes 150, the purpose of which is to accommodate a safety pin, suture or other such fastening means to secure the adapter to a sheet, patient's garment or other article, if found desirable or expedient to do so.

While a toothed edge has been shown as the locking mechanism to secure the connectors against back-off, it will be appreciated that other locking means equivalent in function may be provided.

In like manner, any of the per se known means for placing the syringe or other source of fluid medication in engagement with the syringe connector may be employed, e.g. the outwardly directed luer flange described in the aforementioned U.S. Pat. No. 4,187,848.

While reference throughout the foregoing specification has been made to anesthetic procedures utilizing a syringe to introduce liquid anesthesia into a spinal or epidural catheter, the primary task of this invention, it is to be expressly understood that the invention is not restricted to such procedures. It may be utilized in other cathaterization procedures where a liquid vehicle is introduced via a catheter, which procedures require the catheter to be in fluid communication with a syringe or other source of a liquid drug or other medication.

Other changes may be readily suggested to those skilled in the art in the light of the foregoing description.

What is claimed for:

1. A unitary adapter for placing the proximal end of a catheter which has been inserted in a patient's body in liquid communication with a source of a liquid to be administered from a syringe to said patient by means of said catheter, said adapter comprising:
    a catheter connector housing having distal and proximal ends, said distal end having an opening through which said proximal end of said catheter may be inserted, said catheter connector housing having an internal bore to which said opening communicates;
    an elongated elastomeric and compressible plug seated within said bore adjacent said distal end of said catheter connector in a relatively uncompressed condition, said plug having a channel extending therethrough aligned with said opening in said distal end of said catheter housing, whereby said catheter inserted within said opening can extend within said channel, the inner dimensions of said channel when uncompressed and of said opening being slightly greater than the outer dimensions of said catheter to permit insertion of said catheter therewithin;
    a syringe connector housing having proximal and distal ends and a passageway for said liquid extending longitudinally between said ends thereof, said proximal end having means for releasably engaging the tip of said syringe, said distal end of said source connector housing having an opening communicating with said passageway;
    retaining means inseparably housings together with said proximal end of said catheter connector housing seated within said distal end of said syringe connector housing;
    means for reversibly moving said connectors longitudinally with respect to one another from an open, spaced position permitting insertion and withdrawal of said catheter from said catheter connector to a closed abutting position wherein said passageway in said syringe connector housing, said bore in said catheter connector, said channel in said plug and said catheter when contained therein are in liquid communication to define a closed channel for administering said liquid from said syringe to said patient through said catheter, said means for moving said connector housings between open and closed positions being threads on said proximal end of said catheter connector housing mating with threads on said distal end of said syringe connector housing, whereby said housings can be screwed together to provide said closed position and unscrewed to said open position;
    compression means for compressing said plug when said connector housings are in said closed position, whereby to reduce the gap of said channel and thereby cause said plug to frictionally engage said catheter inserted therein and to retain said catheter in said adapter; and
    locking means for securing said connectors in said closed position, whereby to prevent accidental unscrewing of said connectors toward said open position.

2. An adapter as defined in claim 1 wherein said syringe connector has ratchet-type teeth at its distal end and said locking means comprises a locking wing on the external surface of said catheter connector, the proximal edge of said locking wing engaging one said tooth when said connectors are screwed together to said closed position, said locking wing thereby interfering with a course of said ratchet-type teeth and thereby preventing accidental unscrewing of said connectors.

3. An adapter as defined in claim 1 including means for preventing overtightening of said connectors in said closed position.

4. An adapter as defined in claim 2 including detent means at one end of said teeth for limiting how tightly together said connector housings can be screwed, said locking wing edge engaging the space between said detent means and the tooth adjacent thereto to lock said connectors together to prevent accidental movement.

5. An adapter as defined in claim 1 wherein said retaining means consists of engaged snap rings at superposed ends of said connectors.

6. A unitary adapter for placing the proximal end of a catheter which has been inserted in a patient's body in liquid communication with a source of a liquid to be administered to the patient by means of the catheter, the adapter comprising:
    a catheter connector housing having distal and proximal ends, the distal end having an opening through which the proximal end of said catheter may be inserted, the catheter connector housing having an internal bore to which the opening communicates:

an elongated elastomeric and compressible plug seated within the bore adjacent the distal end of the catheter connector in a relatively uncompressed condition, the plug having a channel extending therethrough aligned with the opening in the distal end of the catheter housing, whereby the catheter inserted within the opening can extend within the channel, the inner dimensions of the channel when uncompressed and of the opening being slightly greater than the outer dimensions of the catheter to permit insertion of said catheter therewithin;

a connector housing for the liquid source means having proximal and distal ends and a passageway for the liquid extending longitudinally between the ends thereof, the proximal end having means for releasably engaging the liquid source means, the distal end of the source connector housing having an opening communicating with the passageway;

retaining means inseparably retaining the housings together with the proximal end of the catheter connector housing seated within the distal end of the liquid source connector housing;

means for reversibly moving the connectors longitudinally with respect to one another from an open, spaced position permitting insertion and withdrawal of the catheter from the catheter connector to a closed abutting position wherein the passageway in the syringe connector housing, the bore in the catheter connector, the channel in the plug and the catheter when contained therein are in liquid communication to define a closed channel for administering the liquid from the liquid source means to the patient through the catheter, wherein said means for moving said connectors between open and closed positions are threads on said proximal end of said catheter connector housing mating with threads on said distal end of said liquid source means connector housing, whereby said housings can be screwed together to provide said closed position and unscrewed to said open position;

compression means for compressing the plug when the connector housings are in closed position, whereby to reduce the gap of the channel and thereby cause the plug to frictionally engage the catheter inserted therein and to retain the catheter in the adapter; and locking means for securing the connectors in the closed position, whereby to prevent accidental unscrewing of said connectors toward the open position, and thereby preventing accidental removal of the catheter from the adapter.

7. An adapter as defined in claim 6 including detent means for limiting how tightly together said housings may be screwed.

8. An adapter as defined in claim 6 wherein the liquid source connector has ratchet-type teeth at its distal end and the locking means for securing the connectors in the closed position consists essentially of a locking wing on the external surface of the catheter connector housing, the proximal edge of the locking wing engaging one of the teeth when the connectors are secured together in the closed position, the locking wing thereby interfering with a course of the ratchet-type teeth, thereby preventing accidental unscrewing of the connectors towards the open position.

* * * * *